(12) United States Patent
Ichigaya

(10) Patent No.: US 6,516,624 B1
(45) Date of Patent: Feb. 11, 2003

(54) COOLING PILLOW

(75) Inventor: Hiroshi Ichigaya, Saitama (JP)

(73) Assignee: Seft Development Laboratory Co., Ltd., Saitama (JP)

( * ) Notice: Subject to any disclaimer, the term of this patent is extended or adjusted under 35 U.S.C. 154(b) by 0 days.

(21) Appl. No.: 09/744,806
(22) PCT Filed: Dec. 28, 1998
(86) PCT No.: PCT/JP98/06000
§ 371 (c)(1), (2), (4) Date: Mar. 12, 2001
(87) PCT Pub. No.: WO00/06006
PCT Pub. Date: Feb. 10, 2000

(30) Foreign Application Priority Data

Jul. 30, 1998 (JP) .......................................... 10-215277
Aug. 25, 1998 (JP) .......................................... 10-238171
Sep. 10, 1998 (JP) .......................................... 10-256859

(51) Int. Cl.[7] .............................................. F25D 23/12
(52) U.S. Cl. ...................................... 62/259.3; 62/261
(58) Field of Search ............................. 62/259.3, 259.4, 62/459.9, 530, 371, 261

(56) References Cited

U.S. PATENT DOCUMENTS 4,325,151 A * 4/1982 Wu ................................ 5/441
4,330,892 A * 5/1982 Fukushima ..................... 5/437
5,632,051 A * 5/1997 Stanley et al. .................. 5/636

* cited by examiner

Primary Examiner—William C. Doerrler
Assistant Examiner—Melvin Jones
(74) Attorney, Agent, or Firm—Rabin & Berdo, P.C.

(57) ABSTRACT

The present invention provides: a cooling pillow which is easy to prepare, whose cooling capability lasts for a long time, which does not require a time-consuming operation such as changing the water, and which is effective in a hard-to-sleep summer night or when one has a fever from a cold; a cooling garment which has a reduced power consumption, allows one to avoid heat with a simple structure, and allows one to be comfortable even in a high temperature environment; and a cooling helmet capable of eliminating the discomfort caused by heat, preventing exhaustion of stamina, lowering of concentration, and lowering of work efficiency, and increasing the safety during work, etc.

The above-described cooling pillow, the-cooling garment and the cooling helmet are all based on a principle that by allowing air to flow in close contact with a fibrous material which is in the vicinity of the body and contains a sufficient amount of water to promote vaporization of water so that the head, the trunk, etc., can be cooled by absorption of the vaporization heat thereupon. Accordingly, they comprise a fan for supplying air, a passageway for passing the air therethrough, a vaporization sheet defining the passageway and containing water, etc.

3 Claims, 14 Drawing Sheets

F I G. 1 0
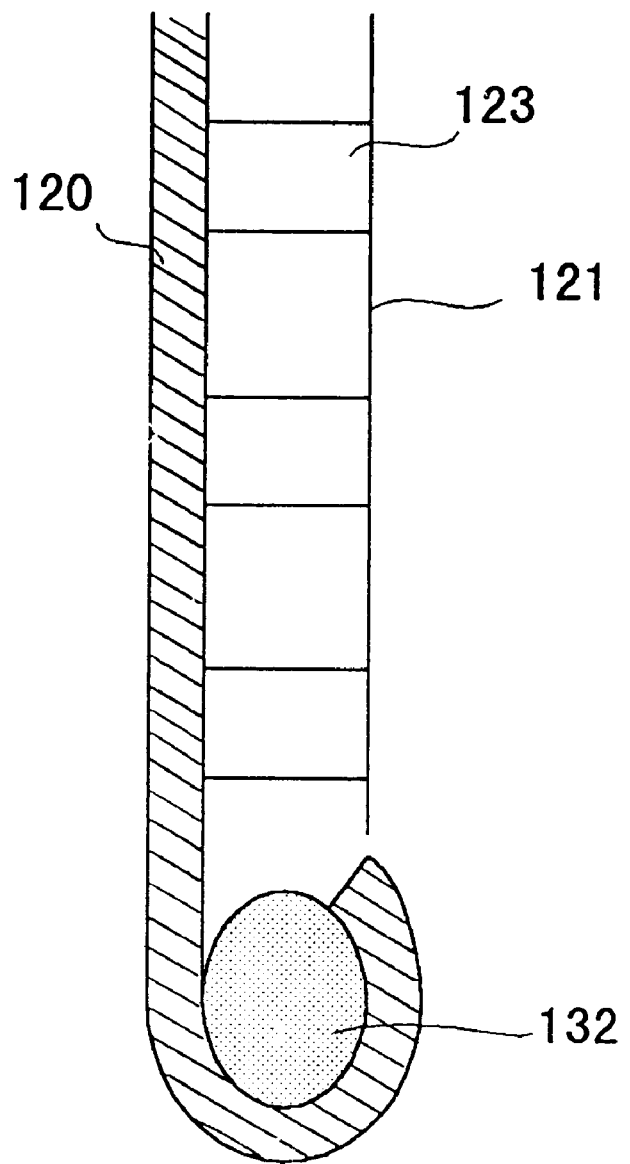

COOLING PILLOW

TECHNICAL FIELD

The present invention relates to a device for cooling the head, the trunk, etc., of a person by utilizing an endothermic effect upon vaporization of water, and particularly to a cooling pillow for ensuring a comfortable sleep in a hot and hard-to-sleep night, a cooling garment for allowing one to be comfortable even in a high temperature environment, and a cooling helmet which can be used as a safety helmet or a motorcycle helmet.

BACKGROUND ART

In a hard-to-sleep summer night or when one has a fever from a cold, a water pillow is used as a means for cooling the head. Ice is sometimes put into a water pillow in addition to water in order to lower the temperature of the water therein so that the water pillow can be used over a long period of time.

When ice is put into a common water pillow, it feels very cool in the beginning, but the temperature gradually increases and the cooling capability decreases. When the temperature of the water therein is about 25° C., it is likely that because it was initially very cool, the user no longer feels the coolness even though it actually still has some cooling effect. Therefore, if one uses a water pillow for the purpose of having a good sleep in a hot midsummer night, it is necessary to frequently change the water or ice therein, which rather disturbs a good sleep.

Water pillows and other types of commercially available cooling pillows for which the coolant therein needs to be frozen in a freezer require preparation in one form or another prior to use.

Moreover, as a measure against heat while one sleeps, it is possible to cool the entire room by using an air conditioner. However, with an air conditioner, the room air and the wall and furniture that are in contact with the air are inevitably cooled, thereby resulting in an increased waste of energy. Moreover, if the economic development of the developing countries continues and the diffusion rate of air conditioners in the developing countries becomes as high as that in the developed countries in the future, the amount of carbon dioxide discharged may then dramatically increase, thereby presenting a significant cause of the global warming.

Under the current circumstances where the global warming has become problematic and it is desired to reduce the use of fossil fuels, it is needless to say that a device for cooling only the body of a person or a main part of the body is preferred over cooling means whose energy consumption or energy waste is substantial such as an air conditioner. Moreover, an air conditioner is a complicated and expensive device, and it is not a device which can be easily installed in any place. Furthermore, an air conditioner can only be used in a room, but cannot be used outdoor.

In many work places such as construction sites, quarries, heavy machinery manufacturing sites, and the like, it is an obligation to wear a helmet during work in order to ensure safety. Moreover, under the Road Traffic Act, it is an obligation to wear a helmet when riding a motorcycle in order to ensure safety.

If one wears a helmet in a hot period in the summer, particularly during work under a burning sun, one feels hot because heat radiation from the head is hindered, and the head becomes humid because of a large amount of perspiration, whereby one feels uncomfortable. If such a condition lasts for some time, it would exhaust one's stamina, lower one's concentration, and lower one's work efficiency. However, even in such situations, in order to preferentially ensure safety, one needs to wear a helmet, and one cannot perform a dangerous operation without wearing a helmet. Also when one rides a motorcycle in a hot period, wearing a helmet may increase the temperature inside the helmet, thereby lowering one's concentration, and thus significantly increasing the danger.

An object of the present invention which has been made in view of the circumstances as described above is to provide a cooling pillow which is easy to prepare, whose cooling capability lasts for a long time, which does not require a time-consuming operation such as changing the water, and which is effective in a hard-to-sleep summer night or when one has a fever from a cold.

Another object of the present invention which has been made in view of the circumstances as described above is to provide a cooling garment which has a reduced power consumption, allows one to avoid heat with a simple structure, and allows one to be comfortable even in a high temperature environment.

Still another object of the present invention which has been made in view of the circumstances as described above is to provide a cooling helmet capable of eliminating the discomfort caused by the heat from wearing a helmet, preventing exhaustion of stamina, lowering of concentration, and lowering of work efficiency, and increasing the safety during work, etc.

DISCLOSURE OF THE INVENTION

A cooling pillow of the first invention comprises: an air passageway serving as a path of air; and a water holding member provided on the air passageway for holding water with at least one side thereof which is in contact with the passageway being wet, wherein the head which is rested on the water holding member directly or via a thermally conductive member is cooled by a vaporization heat which is absorbed upon vaporization of the water held in the water holding member into the air passing through the air passageway.

Preferably, the cooling pillow further comprises passageway; and a water supply section for continuously supplying water to the water holding member by a water absorbing action of the water holding member.

A cooling garment of the second invention comprises: a garment forming material including an inner cloth on a side in contact with a body and an outer cloth on an outer side of the inner cloth, thereby defining an air passageway therebetween; water supply means for supplying water to the inner cloth of the garment forming material; and air supply means for passing air through the air passageway and discharging the air which has been passed therethrough, wherein a wearer is cooled by utilizing a vaporization heat which is taken away when passing the air through the air passageway to vaporize the water supplied to the inner cloth.

One side of the inner cloth which is in contact with the air passageway is made of a fibrous material so that the water supplied from the water supply means is allowed to permeate across an entire area by a capillary phenomenon thereof, and the air supply means is operated in a direction such as to suck in the air which has flown into the air passageway through an opening which is provided in an end portion of the air passageway.

A cooling helmet of the third invention comprises: an outer shell for protecting the head of a wearer; a water guiding member provided on an inner side of the outer shell to define an air passageway between the water guiding member and the outer shell, for allowing water to permeate into a surface thereof on at least one side thereof which is in contact with the air passageway; water supply means for supplying moisture to the water guiding member; and air supply means for passing outside air through the air passageway, wherein the head of the wearer is cooled by vaporizing the moisture contained in the water guiding member as the air flows through the air passageway.

The water supply means is provided along a lower circumference of the outer shell, and the water guiding member allows the water which is sucked up from the water supply means to permeate into a side thereof which is in contact with the air passageway by a capillary phenomenon.

BRIEF DESCRIPTION OF THE DRAWINGS

FIG. 10 is a cross-sectional view illustrating a lower end portion of the cooling garment.

BEST MODE FOR CARRYING OUT THE INVENTION

Best modes for carrying out the invention of the present application will now be described with reference to the figures.

First Embodiment

Figure 1:
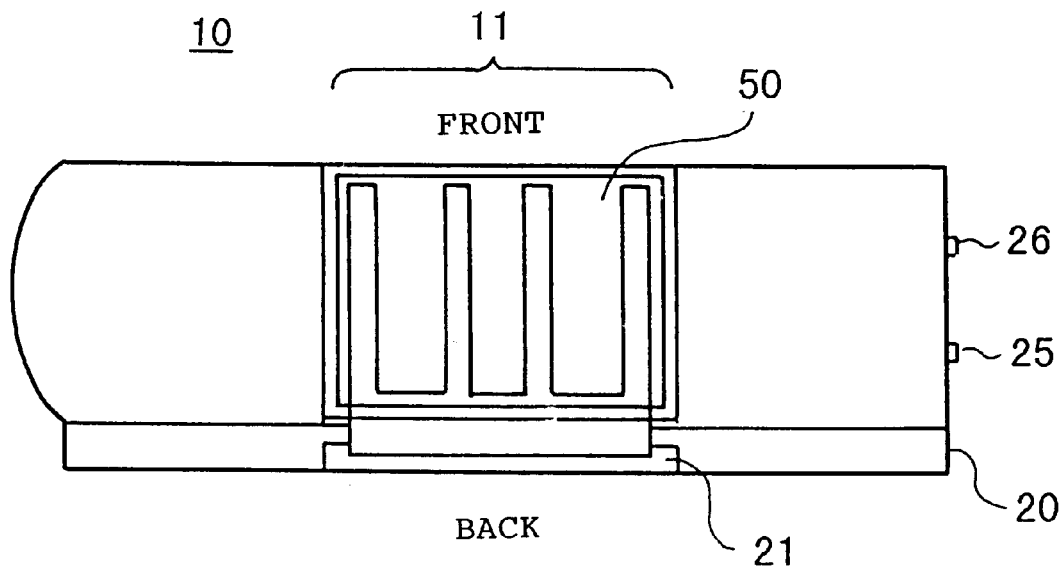
FIG. 1 is a plan view illustrating a cooling pillow according to the first embodiment as viewed from above.
Figure 2:
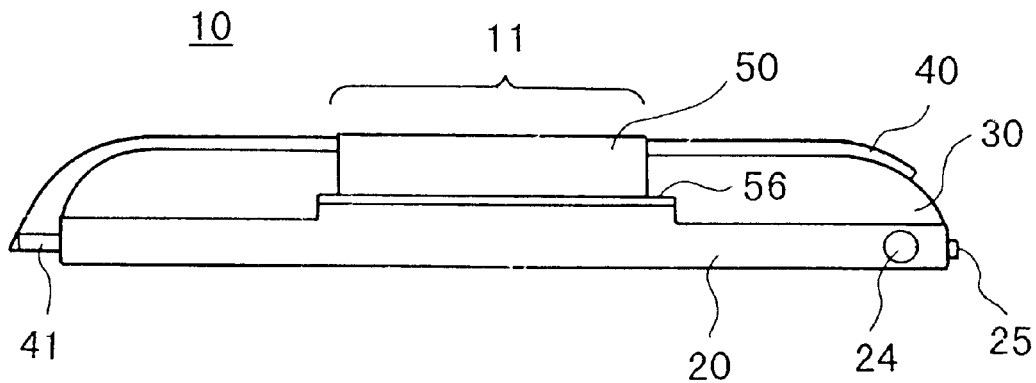
FIG. 2 illustrates the cooling pillow of FIG. 1 as viewed from the back side.
Figure 3:
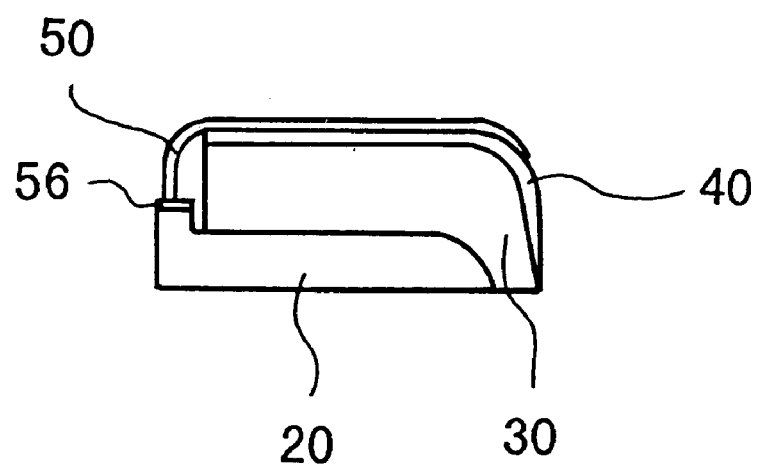
FIG. 3 is a cross-sectional view illustrating a central portion of the cooling pillow.

FIG. 1 is a plan view illustrating a cooling pillow according to the first embodiment of the present invention as viewed from above, and FIG. 2 illustrates the cooling pillow of FIG. 1 as viewed from the back side. In a cooling pillow 10 illustrated in FIGS. 1 and 2, a central portion indicated by reference numeral 11 is the portion on which a person rests the head while in bed. By a function to be described later, the temperature of the central portion 11 is lowered, thereby cooling the head rested thereon. A tank 20 to be filled with water is provided in a lower portion of the cooling pillow 10, and a cushioning material 30 is provided thereon. While the cushioning material 30 is provided for the purpose of improving the degree of comfort during sleep while in bed, it is not essential to the present invention. The tank 20 corresponds to the water supply section of the present invention.

An air passageway 40 is placed on the cushioning material 30. One end of a vaporization sheet 50 is placed on a portion of the air passageway 40 over the central portion 11, and the other end of the vaporization sheet 50 is inserted into the tank 20 via a slit 21 provided in the tank 20 described above, and is immersed in the water therein.

The air passageway 40 provides a path for passing therethrough the air which is supplied from a fan 41 provided on one side of the cooling pillow 10 (the left side in FIGS. 1 and 2). The fan 41 corresponds to the air supply means of the present invention. The air which has passed through the air passageway 40 is discharged to the outside from the side opposite to the fan 41 (the right side in FIGS. 1 and 2).

Figure 4:
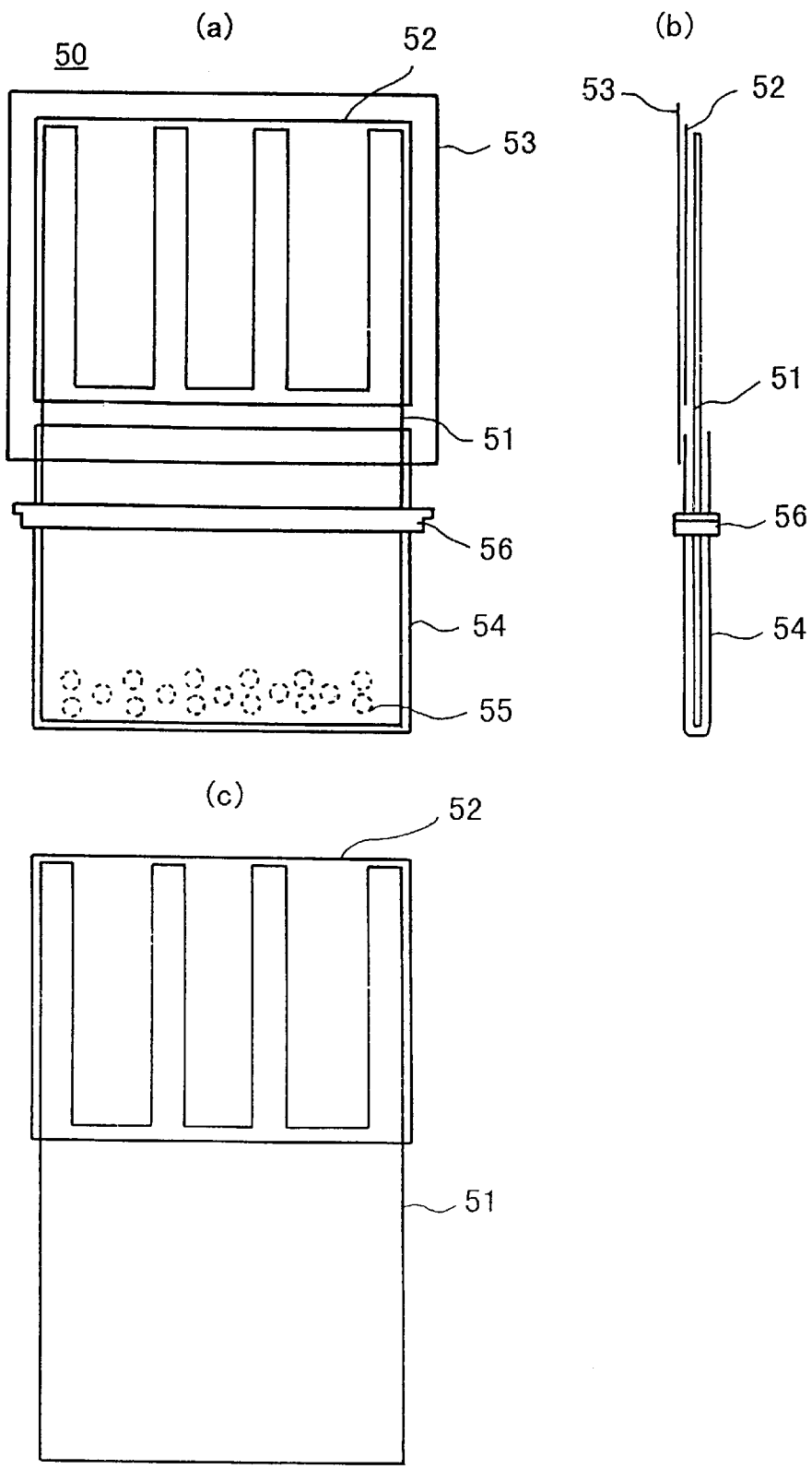
FIG. 4 shows a general view of a vaporization sheet, a cross-sectional view of the vaporization sheet, and a water guiding cloth forming the vaporization sheet.

Now, referring to FIG. 4, the vaporization sheet 50 will be described. The main body of the vaporization sheet 50 is a water guiding cloth 51 as illustrated in FIG. 4(c). The water guiding cloth 51 corresponds to the water holding member of the present invention. The water guiding cloth 51 may be a towel cloth, for example. A towel cloth is excellent in sucking up water and holding the water sucked up. A lower portion of the water guiding cloth 51 as illustrated in FIG. 4(c) is covered by a water guiding cloth cover 54 made of a polyethylene. The lower end portion of the water guiding cloth cover 54 is provided with many water absorbing holes 55.

When the lower portion of the water guiding cloth 51 which is covered by the water guiding cloth cover 54 is inserted into the tank 20, the water guiding cloth 51 absorbs water through the water absorbing holes 55 and sucks up the water by the capillary phenomenon. The water guiding cloth cover 54 serves to prevent unnecessary vaporization of water being sucked up and to prevent the cushioning material 30 from being wet The lower portion of the water guiding cloth 51, being covered by the water guiding cloth cover 54, is passed through a connector 56. The connector 56 can be attached/detached to/from the slit 21 of the tank 20, thereby facilitating the insertion of the water guiding cloth 51 into the tank 20.

The upper portion of the water guiding cloth 51 is formed in a comb-like pattern. A thin cloth 52 having a high water permeability is attached to this portion. The thin cloth 52 and the comb-like portion of the water guiding cloth 51 are placed on the air passageway 40 via a meshed material 43 to be described later. The water sucked up from the lower side of the water guiding cloth 51 is transferred via the upper comb-like portion thereof to the thin cloth 52, and the water is dispersed and quickly spread across the entire thin cloth 52. The comb-like portion of the water guiding cloth 51 and the thin cloth 52 placed on the air passageway 40 are further covered by a water-proof sheet 53, thereby preventing the head rested thereon from being wet. The water guiding cloth 51, the thin cloth 52 and the water-proof sheet 53 may be separate components to be assembled together as described above, or may alternatively be a single pre-integrated component. With the vaporization sheet 50 having the structure as described above, when the lower end portion of the water guiding cloth 51 is inserted into the tank 20, the thin cloth 52 becomes entirely wet in about 10 minutes.

After using the vaporization sheet 50 over a long period of time, residue materials contained in tap water are concentrated and accumulated in the water guiding cloth 51 and the thin cloth 52, whereby water is not easily vaporized and the cooling effect decreases. Therefore, it is desirable to periodically replace the vaporization sheet 50. In order to facilitate the replacement, the vaporization sheet 50 is detachably attached to a portion of the air passageway 40 over the central portion 1 by means of, for example, a double-sided adhesive tape or a magic tape.

Next, the principle based on which the cooling pillow 10 of the present embodiment cools the head will be described. As described above, the fan 41 is provided on one side of the cooling pillow 10. The fan 41 takes in the room air from the lower side and supplies the air upward. The air passes through the air passageway 40 provided on the cushioning material 30, and is discharged to the outside from the side opposite to the fan.

Figure 5:
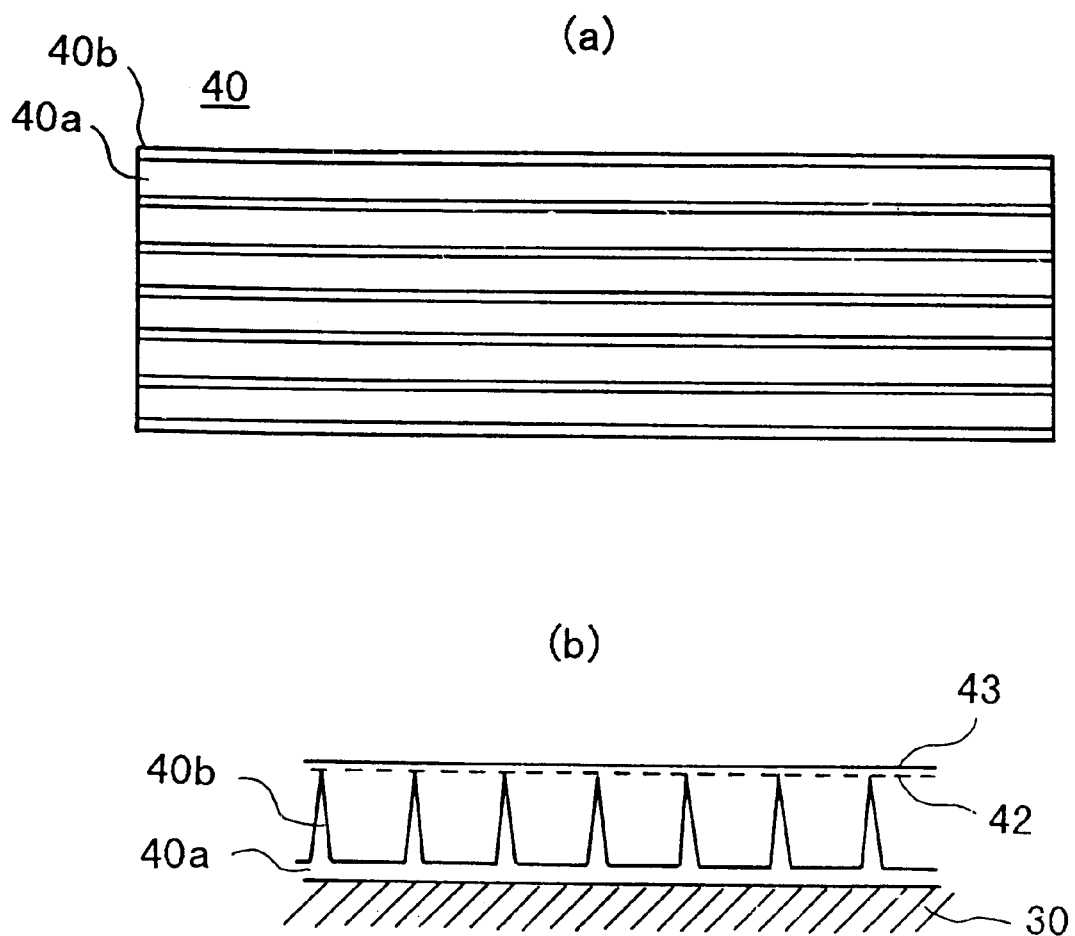
FIG. 5 shows a plan view illustrating an air passageway as viewed from above, and a cross-sectional view illustrating the air passage.

FIG. 5(*a*) is a plan view illustrating the air passageway 40 as viewed from above, and FIG. 5(*b*) illustrates a part of a transverse section of the air passageway 40. The air passageway 40 has a structure including a rubber-made plate 40*a* and many linear protrusions 40*b* thereon running longitudinally across the cooling pillow 10. The air passageway 40 is placed on the cushioning material 30, and the meshed material 42 having many holes therein is laid over the entire air passageway 40. Moreover, an upper cloth 43 is placed over the meshed material 42 except for the central portion 11. The protrusions 40*b* have a height of about 10 mm and an interval of also about 10 mm between protrusions.

The upper cloth 43 may be a high density cotton cloth which is used in down jackets, for example. This is a cloth which is woven with about 300 filaments of cotton yarn per centimeter, and is substantially impermeable to air with a pressure as much as that created by the fan used in the present embodiment. Therefore, in portions over which the upper cloth 43 is placed, the upper portion of the space between adjacent protrusions is closed by the upper cloth 43, so that the air flowing therethrough does not escape upward and the majority of the air passes through the cooling pillow 10 from left to right.

In the central portion 11, on the other hand, the comb-like portion on the upper side of the water guiding cloth 51 and the thin cloth 52 attached thereto are placed directly on the meshed material 43, and the water-proof sheet 53 is further placed thereon. Since the meshed material 43 is provided with many holes as described above, the air passing thereunder closely contacts with the thin cloth 52. The contact between the air and the thin cloth 52 promotes vaporization of the moisture which is held in the thin cloth 52. The vaporized moisture is carried to the outside along with the air passing therethrough. Since water, upon vaporization into gaseous molecules, takes the vaporization heat away from the ambient-water molecules, the temperature of the moisture held in the thin cloth 52 decreases. Thus, the head which is in contact with the thin cloth 52 via the water-proof sheet 53 is cooled, whereby the sleeping person feels the head being cool.

It can be said that this system is an application of the perspiration-based cooling function inherent to higher animals, that is, the function of perspiring when it is hot so as to cool the body by the vaporization heat which is taken away upon vaporization of the moisture.

In the system of the present embodiment, the amount of vaporization of water (corresponding to the amount of perspiration of animals) can be freely controlled by varying the amount of air flow. Moreover, in the case of perspiration, when there is only a little air flow, the moisture may not be vaporized but rather be wasted by running down as sweat, and this may even cause a discomfort by making the bedclothes wet. In contrast, with the system of the present embodiment, such a problem associated with the perspiration does not occur because substantially 100% of the moisture is vaporized.

Moreover, while the vaporization heat taken away through perspiration of a person or an animal decreases not only the temperature of the skin but also the temperature of the evaporated moisture, the cooled moisture has substantially no contribution to the cooling of the body but is directly dissipated into the air. In contrast, with the system of the present embodiment, the moisture in the vaporization sheet cooled upon vaporization closely contacts with the air flowing through the air passageway 40 to also cool the air. In other words, the endothermic effect based on vaporization of water acts in two forms, i.e., the cooling of the vaporization sheet 50 and the cooling of the air in the air passageway 40. If the air in the air passageway 40 is cooled, the temperature gradient near the head becomes very large because the location of the air passageway 40 is very close to the head. If the temperature gradient is large, the heat radiation is promoted, whereby an additional coolness is felt by a person.

With regard to the action of cooling the air in the air passageway 40, thereby promoting the heat-radiation from the head, an actual observation shows that when the fan 41 is operated with an appropriate rotational speed to measure the temperature of the air discharged through the air passageway 40, the temperature is slightly higher than the room temperature. This suggests that when the room temperature is 28° C., for example, the air in the vicinity of the thin cloth 52 is once cooled by the cooled water to about 24° C., for example, but is warmed up again by the heat of the head (about 37° C.) to about 29° C. Thus, the increase in the temperature of the air means that the head is cooled. Since the thin cloth 52 and the water-proof sheet 53 use very thin materials, they have a small heat resistance and a good thermal conductivity. This further enhances the effect described above.

Vaporization of 1 cc of water takes away a heat of about 580 calories. Therefore, if even a little vaporization continues, a considerable coolness lasts. When the amount of air to be passed is set to about 0.2 liter per second, for example, about 20 to 30 cc of water is vaporized overnight. When 30 cc of water is consumed while one is sleeping (about 8 hours), a heat of about 17 kilocalories is absorbed. This is substantially equivalent to a 10° C. increase in the water temperature of a 1.7-liter water pillow. Since the coolness effectively lasts for this period of time, the portion on which the head is rested would not be warmed up by the temperature of the head. The power consumption required for the fan to supply air at such a flow rate is as small as about 0.2 watt. Although the noise from the fan is very low due to such a small power consumption, slight rotation sound can be heard if the fan is used by itself because it is near the ears. If the rotation sound is disturbing, the sound can be blocked by using a sound insulation device. In such a case, the sound can be substantially completely blocked with a simple sound insulation device because the volume of the original sound is low. Moreover, when the capacity of the tank 20 is about 1000 cc, one does not need to refill the tank 20 with water for a few ten days once the tank 20 is filled up with water.

Figure 6:
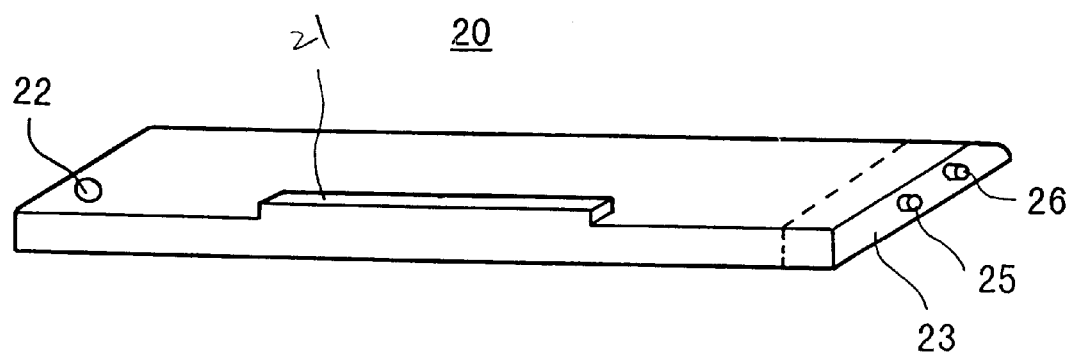
FIG. 6 is a perspective view illustrating a tank.

FIG. 6 is a perspective view illustrating the tank 20. The tank 20 is provided with the slit 21. As described above, the slit 21 is such that the connector 56, with the lower portion of the water guiding cloth 51 being passed therethrough, can be easily attached thereto. The slit 21 portion is located to be somewhat higher than the other portions therearound so that the water therein is not easily spilt over. Water is charged into the tank 20 through a water injection hole 22. On the right side of the tank 20, there is provided a circuit box 23 including a battery 24 for supplying an electric power to the fan 41, a volume control 25 for adjusting the rotational speed of the fan, a power switch 26, and other necessary circuits.

Various modifications can be made to the cooling pillow of the embodiment described above. For example, while a fan for supplying the room air through the air passageway is provided in the embodiment described above, there is some air flow even without the fan because there is usually a convection current of air in a room. By utilizing the air flow, the vaporization of the water contained in the water holding member is actively effectuated to some degree to cool the head even without the fan, especially under low-humidity circumstances. Therefore, under such circumstances, the fan is not essential. Moreover, while the vaporization sheet and the air passageway are provided for cooling only in the pillow in the present embodiment, the vaporization sheet and the air passageway can be extended to the shoulder and/or the back as necessary so as to simultaneously cool these parts.

While the present invention effectively utilizes the phenomenon that water, upon vaporization, takes the vaporization heat away from the ambient to lower the ambient temperature, the principle itself, substantially as it is, can also be applied to things other than a pillow.

For example, floor cushions for pets that are currently commercially available include those in which a wrung-out wet towel is placed in a position where the pet sits and those in which a material such as a polymer having a high water absorptivity is allowed to absorb water and is placed in a position where the pet sits. When a pet feels hot, the pet can sit on it to feel cool. However, after passage of a certain period of time, the portion on which the pet has sat is warmed up by the temperature of the pet and the pet is unlikely to feel cool any more. In view of this, as in the embodiment described above, an air passageway can be provided in a position where the pet sits, with a water holding member thereon for holding water while at least one side thereof that is in contact with the air passageway is wet, and the air can be passed through the air passageway by using air supply means such as a fan so as to promote vaporization of the water which is held in the water holding member, thereby cooling the pet that is sitting thereon.

Similarly, the present invention is widely applicable to things which are used in close contact with the body such as, for example, seats of automobiles, buses, trains, etc., sofas for use in a room, floor cushions on which a person sits, futon mats, etc., as well as pillows and floor cushions for pets. It is understood that they also fall within the technical scope of the present invention.

As described above, the cooling pillow of the present invention cools the head by utilizing the heat of vaporization of water, whereby it is possible to provide a cooling pillow which has a certain cooling capability lasting for a long time, which does not require a time-consuming operation such as changing the water, which does not require a time-consuming operation such as cooling it in advance in a refrigerator, and which is suitable for use in a hard-to-sleep summer night or when one has a fever from a cold.

Second Embodiment

Figure 7:
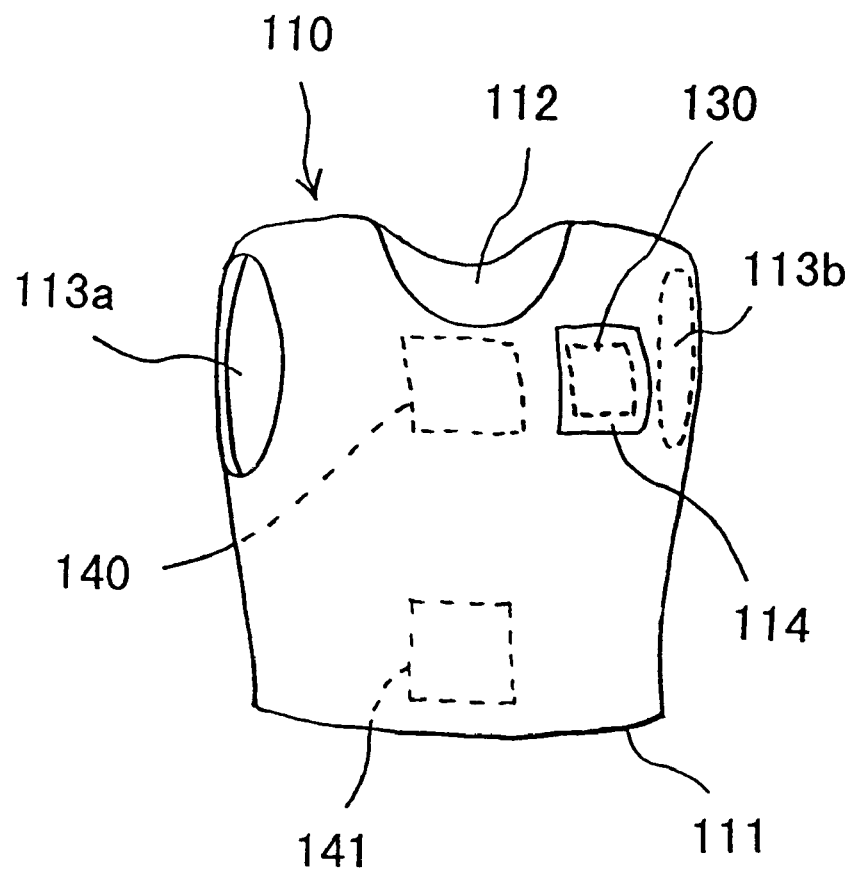
FIG. 7 is a perspective view illustrating a cooling garment according to the second embodiment.
Figure 11:
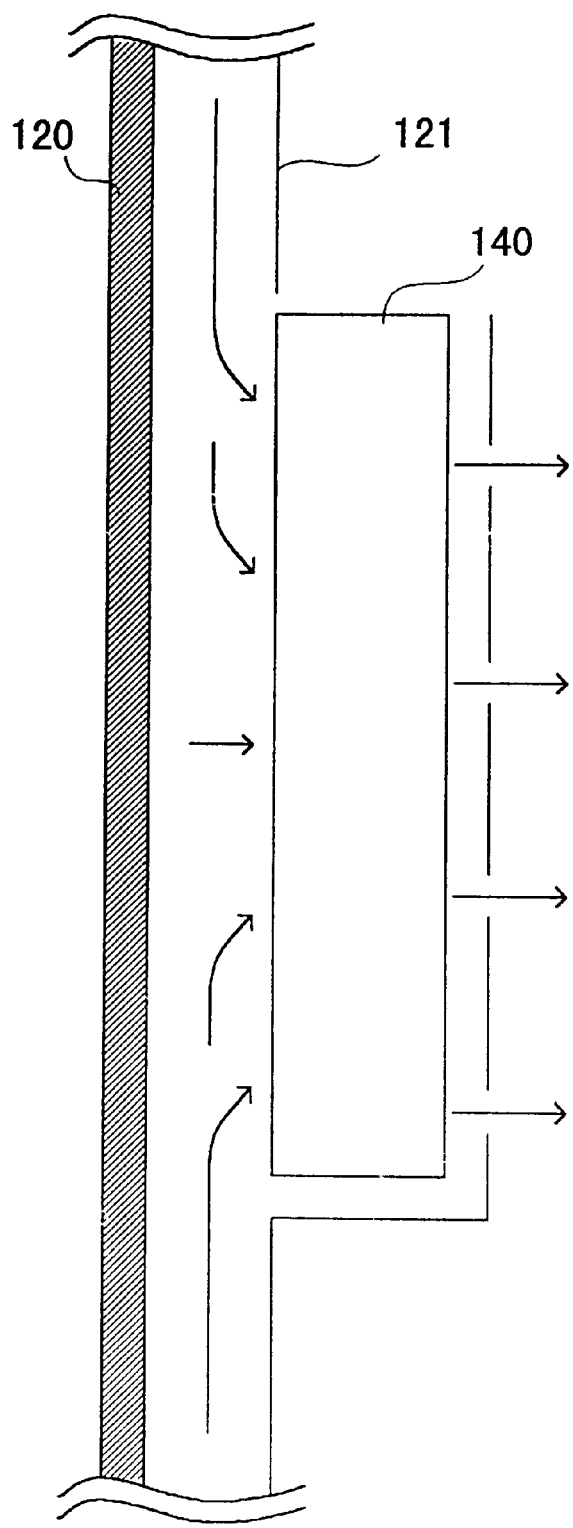
FIG. 11 is a cross-sectional view illustrating a part to which a fan is attached.

Next, the second embodiment of the present invention will be described. FIG. 7 is a perspective view illustrating a cooling garment according to the second embodiment, FIG. 8 illustrates an enlarged cross section of a material forming the cooling garment, FIG. 9 is a cross-sectional view illustrating a pocket with a sponge being inserted therein, FIG. 10 is a cross-sectional view illustrating a lower end portion of the cooling garment, and FIG. 11 is a cross-sectional view illustrating a part to which a fan is attached.

As illustrated in FIG. 7., a cooling garment 110 of the present embodiment is a sleeveless vest-shaped garment, and it can be worn by passing the head and the arms through the lower end opening 111, and further passing the head through the upper end opening 112 and-the arms through the openings 113a and 113b on opposite sides, so as to substantially fit to the upper half of the body. Note that the garment may be different types of garments in which the front side thereof is closed by means of buttons or a fastener.

Figure 8:
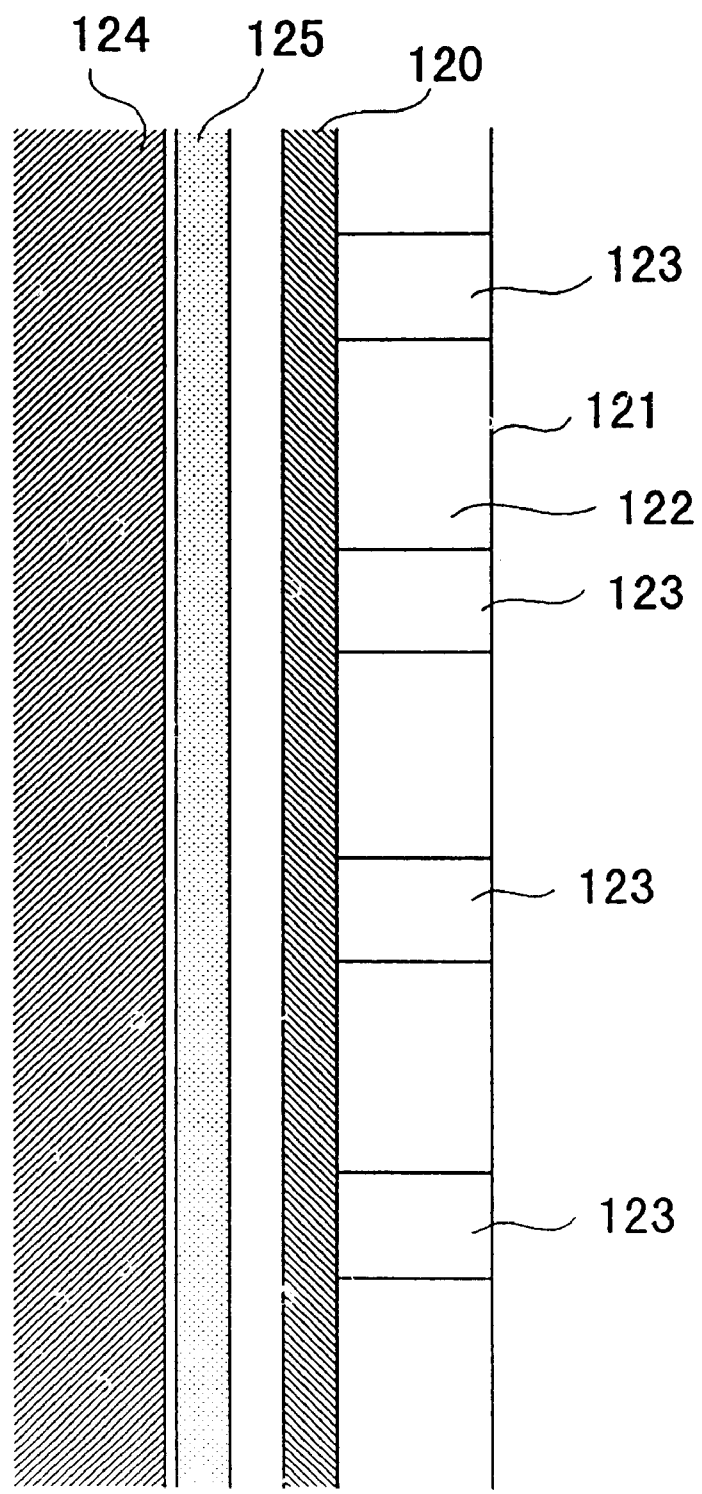
FIG. 8 illustrates an enlarged cross section of a material forming the cooling garment.
Figure 9:
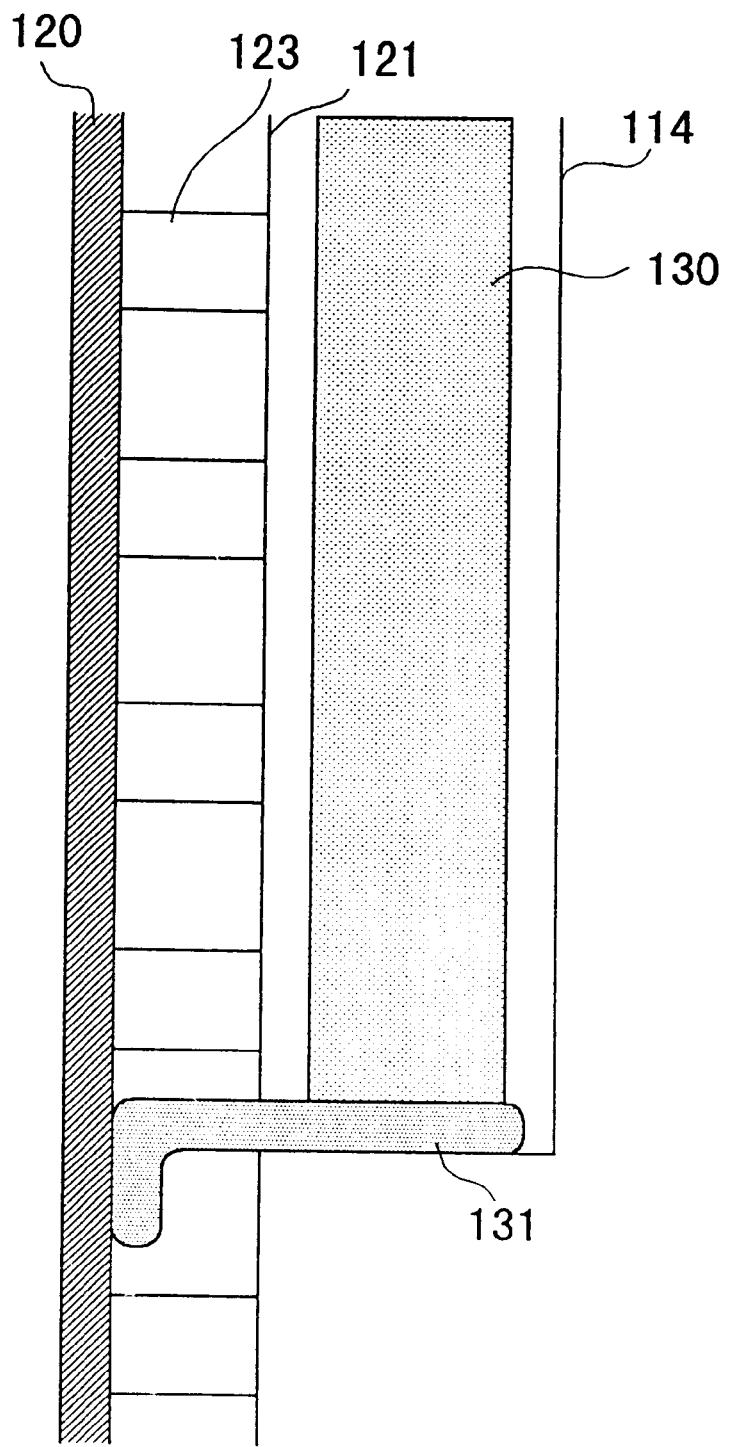
FIG. 9 is a cross-sectional view illustrating a pocket with a sponge being inserted therein.

The material forming the cooling garment 10 is composed of an inner cloth 120 closer to the body surface and an outer cloth 121 on the outside thereof, as illustrated in FIG. 8, with many spacers 123 between the inner cloth 120 and the outer cloth 121 keeping the interval therebetween substantially constantly and defining air passageways 122 therebetween. The cooling garment 110 is normally worn by first wearing an underwear 125 on the bare skin 124, as illustrated in FIG. 8, and then wearing the cooling garment 110 on the underwear 125. In the cooling garment 110, the air passageways 122 are opened to the outside in the bottom portion, the neck portion and the portion between the shoulder and the armpit as illustrated in FIG. 7, and the outside air flows into the air passageways 122 through these portions as will be described later.

The outer side of the inner cloth 120, i.e., the side facing the air passageways 122, is formed by a fine fibrous material so that when water is supplied thereto, the water is immediately diffused in all directions by the capillary phenomenon. On the contrary, the inner side of the inner cloth 120 is waterproofed so that even if water permeates into the outer side, the water is not passed to the inner side. Alternative to the cloth whose inner side is waterproofed, the inner cloth 120 may be formed by an ordinary cloth which diffuses water therethrough with a water-impermeable material such as a vinyl being placed over one side thereof (the side to be the inner side).

The outer cloth 121 may be, for example, the high density cotton cloth as mentioned in the first embodiment. The high density cotton cloth is a cloth which is woven with about 300 filaments of cotton yarn per centimeter, whereby it is substantially impermeable to air even if there is some pressure difference between opposite sides thereon. Therefore, of all the air flowing through the air passageways 122, only a very little air leaks to the outside through the outer cloth 121. However, since the pressure applied to the air flowing through the air passageways 122 is very small as will be described later, it is possible to use a common cotton cloth in place of the high density cotton cloth.

If such a cotton-made material is used for the outer cloth 121, the selection of color or pattern is widened, thereby allowing for a free design in view of the latest fashion to provide cooling garments of various designs.

The spacers 123 defining the air passageways 122 between the inner cloth 120 and the outer cloth 121 are each formed from a cylindrical flexible sponge having a diameter of 3 mm across the bottom surface and a height of 5 mm. The inner cloth 120 and the spacers 123, and the outer cloth 121 and the spacers 123 are bonded together by using an adhesive in the following manner.

First, a 5 mm thick plate-shaped sponge of an appropriate size is provided, and an appropriate amount of adhesive is applied to both sides and allowed to cure so as to form a hard adhesive film on each side of the sponge. The adhesive may be, for example, Aron Melt 110P80HH manufactured by TOA Kagaku Kogyo K.K. The thus obtained sponge is punched through with an appropriate die to produce many cylindrical sponge-made spacers 13 each having a diameter of 3 mm and a height of 5 mm. The strong film of adhesive as described above is applied to opposite bottom surfaces of each spacer 113.

Figure 12:
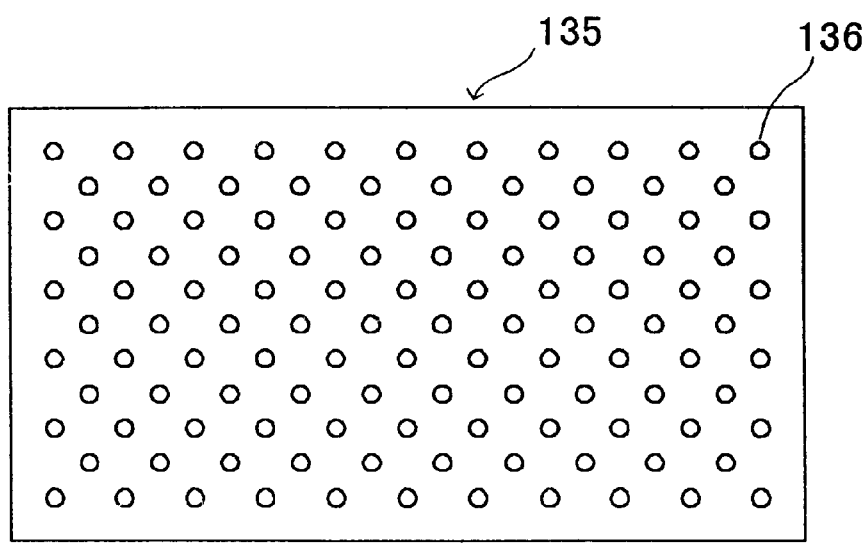
FIG. 12 is a perspective view illustrating a jig for uniformly arranging spacers between an inner cloth and an outer cloth.

Then, a jig 135 as illustrated in FIG. 12 is provided. The jig 135 is provided with many through holes 136 each having a thickness of about 4 mm and a diameter of about 3.1 mm which are in a zigzag pattern with an appropriate interval, for example, 20 mm. The jig 135 is placed on a flat base, and the spacers 123 are inserted one by one into each hole of the jig, after which the inner cloth 120 is laid over the jig 135 so that the inner side thereof (the side of the fibrous material) is in contact with the spacers 123, and the entire area is heated with an iron, or the like. Although the heat temporarily melts the adhesive on one side of each spacer 123 being ironed, the adhesive is cured again after a while with the iron taken away. Thus, the spacers 123 and the inner cloth 120 are firmly bonded together.

Once the spacers 123 and the inner cloth 120 are firmly bonded together, the jig 135 and the inner cloth 120 are turned over as they are, the jig 135 is removed, and the outer cloth 121 is placed thereon and heated with an iron as described above so that the outer cloth 121 and the spacers 123 are bonded together. Thus, there is obtained a material in which many spacers 123 are arranged in a zigzag pattern with an interval of 20 mm, thereby defining the air passageways 122 between the inner cloth 120 and the outer cloth 121. Thus, by using the jig 135, many spacers 123 can be bonded all at once and easily to the inner cloth 120 and to the outer cloth 121.

If the spacers 123 are arranged in a zigzag pattern with an interval of 20 mm as described above, there is provided a sufficient strength to withstand a force which is externally applied under normal situations. For example, even if one, wearing a cooling garment made from this material, sits on a chair leaning against the back of the chair, the air passageways would not be squashed down. Note that the arrangement interval or the arrangement pattern of the spacers 123 and the size of the spacers 123 as described above are merely illustrative, and may optionally be changed according to the application of the cooling garment 110 and/or on which part of the body it is used.

A pocket 114 is provided in the breast portion of the cooling garment 110. The inside of the pocket 114 either is made from a water-impermeable material, includes therein a water-impermeable material such as a vinyl, or is waterproofed. It is so designed that a sponge 130 can be inserted therein as illustrated in FIG. 9. The sponge 130 may be, for example, one which is made of a PVA (polyvinyl alcohol) capable of absorbing a large amount of water. A water guiding piece 131 is provided in the lower end portion of the pocket 114 as illustrated in FIG. 9. This is provided for guiding water which is contained in the sponge 130 to the outer side of the inner cloth 120, i.e., the side thereof which faces and contacts the air passageways 122. Therefore, the water contained in the sponge 130 is supplied to the inner cloth 120 through the water guiding piece 131. Once water is supplied to the inner cloth 120, the water is immediately diffused around by the capillary phenomenon of the fine fibrous material on the outer side as described above.

Since tap water contains impurities such as bleaching powder, it is believed that after using the cooling garment 110 with tap water over a long period of time, the impurities such as bleaching powder contained in tap water precipitate, whereby water cannot easily permeate through the inner cloth 120. In order to prevent this, impurity removing means made of an ion exchange resin, or the like, may be provided in the lower end portion of the pocket 114 or in an appropriate location in the water guiding piece 131 through which water passes so as to prevent the impurity from spreading into the inner cloth 120. In such a case, the impurity removing means is desirably replaceable.

The pocket 114 is provided in the breast portion of the cooling garment 110 and thus is located in a relatively high position as worn by a person. Therefore, when water is guided from the sponge 130 in the pocket 114 to the inner cloth 120, the water is quickly spread allover by virtue of not only the capillary phenomenon but also the influence of gravity. Once water is spread substantially entirely across the inner cloth 120, the osmotic force by the capillary phenomenon is saturated and thus suppressed, but the influence of gravity continues to exist, whereby the water density is greater in a position closer to the lower end portion of the cooling garment 110, and water may drip from the lower end portion. In view of this, a PVA sponge 132 in the form of a belt is attached around the entire periphery of the lower end portion of the inner cloth 120 as illustrated in FIG. 10. By allowing the PVA sponge 132 to absorb any extra-water permeating from above, it is possible to prevent the water from dripping.

As illustrated in FIGS. 7 and 11, a fan 140 to serve as the air supply means is attached to the back surface of the cooling garment 110. A battery 141 to serves as a power source for the fan 140 is attached to the cooling garment 110 below the fan 140 as illustrated in FIG. 7. Note that when employing the types of garments in which the front side thereof is closed by means of buttons or a fastener as described above, it is desirable to provide two fans in left-right symmetry in upper portions on the back or in shoulder portions.

The fan 140 is rotated in a direction such as to draw out the air from the air passageways 122 of the cooling garment 110 as illustrated in FIG. 11. By rotating the fan 140 in this direction, the pressure in the air passageways 122 decreases, thereby making air flow into the air passageways 122 through the openings provided in the bottom portion, the neck portion and the portion between the shoulder and the armpit. The air circulates across the entire cooling garment 110 and then reaches the fan 140 portion to be sucked by the fan 140 and discharged to the outside.

The air passing through the air passageways 122 closely contacts, as it passes therethrough, with the water which has permeated into the inner cloth 120,: thereby promoting vaporization of the moisture. The water, upon vaporization, takes the vaporization heat away from the ambient to lower the ambient temperature. As mentioned above, the amount of heat taken away by water upon vaporization is about 580 calories per 1 cc. Therefore, even if only a little water is vaporized, there is provided a considerable cooling effect. Moreover, since air flows in through many openings to uniformly pass through the entire air passageways 122, moisture is vaporized substantially uniformly across the entire cooling garment 110. Therefore, the temperature of the inner cloth 120 rapidly and uniformly decreases after the start of operation of the fan 140.

If the fan 140 is rotated in a direction such as to supply air into the air passageways 122, a strong air flow hits the inner cloth 120 in the vicinity of the fan 140, whereby a large amount of moisture is vaporized to increase the humidity of the air in this area. Thus, as the air further passes through the air passageways 122, the air is no longer capable of sufficiently vaporizing water, resulting in a non-uniformity in the amount of water vaporized and thus a non-uniformity in the cooling effect.

The way a person, being a homeothermal animal, feels the temperature is substantially influenced by the ambient temperature gradient. For example, even when there is a heat source whose temperature is much lower than the body temperature (about 37° C.) (a heat sink), if the heat source is far away from the body, the temperature gradient in the vicinity of the body surface is small, whereby it is not felt so cool. In contrast, if the heat sink is near the body surface even when the difference between the temperature of the heat sink and the body temperature is not so large, the temperature gradient in the vicinity of the body surface is large, whereby it is felt cool. Experiments show that a person performing light work feels most comfortable when there is a temperature gradient such that the temperature about a few mm away from the body surface is about 31° C.

If one wears the cooling garment 110 of the present embodiment under an environment where the ambient temperature is 35° C. and the humidity is 70%, with an appropriate amount of air being supplied, it is possible to lower the temperature of the inner cloth 120 by about 5 to 6° C. Since the inner cloth 120 is located about a few mm away from the body surface, if the temperature of such a location is lowered by 5 to 6° C., the temperature gradient in the vicinity of the body surface is substantially increased, whereby the wearer feels very cool. Therefore, when staying indoor, an air conditioner is no longer necessary. Moreover, the cooling garment 110 of the present embodiment has an advantage in that it can be worn outdoor. Thus, by wearing the cooling garment 110, one can be comfortable even when having an outdoor activity during a hot season.

Moreover, by changing the rotational speed of the fan 140 or by turning ON/OFF the fan at certain time intervals and changing the time intervals, the way the cooling garment 110 is cooled also changes. Thus, it is possible to adjust the rotational speed or the ON/OFF time intervals of the fan 140 according to the ambient temperature or the type of activity so that one can feel most comfortable.

Furthermore, with the cooling garment 110 of the present embodiment, a cooling effect can be obtained only by supplying air by means of the fan 140 without supplying the inner cloth 120 with water when the ambient temperature is not so high. This is because as discussed above the temperature gradient in the vicinity of the body surface substantially influences how a person feels the temperature. When there is a person in a room with only a little convection current of air, the ambient temperature gradually decreases from the body surface temperature of about 37° C. away from the body, whereby the temperature gradient is not so large. In contrast, if one wears the cooling garment 110 of the present embodiment while the fan 140 is operated at a sufficient rotational speed without supplying the inner cloth 120 with water, the temperature in the immediate vicinity of the body surface is substantially equal to the room temperature even though the cooling effect from vaporization of water is not effectuated. Therefore, the temperature gradient in the vicinity of the body surface is considerably large, whereby the wearer feels considerably cool only by supplying air by means of the fan 140.

If the cooling garment of the present embodiment becomes sufficiently widespread, it is possible to suppress the power consumption by the entire society, particularly the power consumption during the summer when the electric power demand increases, also leading to suppression of the amount of carbon dioxide discharged from the burning of fossil fuels. Moreover, since the structure of the cooling garment is very simple, the production cost therefor is very low. Therefore, it can become widespread in the developing countries. Particularly, if it becomes widespread in the developing countries many of which are in tropical and subtropical regions, it is expected that the demand for air conditioners will not be so high even when these countries economically develop to be as competitive as the developed countries, thereby providing some contribution to the global suppression of the increase in the amount of carbon dioxide discharged.

With the cooling being uniformly provided across the upper half of the body, there may be some parts of the body for which the cooling is excessive. In such a case, a water-impermeable material may be used on one side, facing the air passageways, of a portion of the inner cloth 120 which corresponds to the abdomen, for example, or the inner cloth 120 may be partially cut away for the portion which corresponds to the abdomen. Moreover, holes may be provided in some positions of the inner cloth 120 so that the sweat from working or exercising outdoor can escape therethrough. If the inner cloth 120 is provided with holes, a portion immediately above the underwear comes to serve as the air passageways 122 and contacts with the air passing therethrough. Therefore, by providing the inner cloth 120 with holes, one can also expect an effect of quickly drying underwear which is wet with sweat.

As mentioned above, the amount of heat taken away by 1 cc of water upon vaporization is about 580 calories. Therefore, cooling of 10 Kcal per hour as described above can be achieved only by vaporizing 17.2 cc of water per hour. A calculation shows that the amount of air that should be passed in order to vaporize such an amount of water is about 1 liter per second, though it depends on the temperature and humidity conditions. Many fans that are capable of passing such an amount of air are commercially available, and those having a considerably small size can be obtained.

With the length of the spacers 23 being 5 mm, even for those which can be worn by a person of an average size, the pressure difference between the inside and the outside of the air passageways 122 is not so large, and it is therefore believed that the power consumption of the fan 140 can be suppressed to be about 1 watt. Some of the secondary batteries used in video cameras for household use can last for about 10 hours while supplying an electric power of a few watts. If such secondary batteries are used as the battery 141 for the fan 140, the duration of the battery can be 10 hours or longer, while the total weight of the fan 140 and the battery 141 together can be suppressed to be a few hundred grams or less. Therefore, in normal conditions of use, once the battery is charged, it does not have to be recharged while the user is out the door, and it is unlikely to interfere with an outdoor activity.

Figure 13:
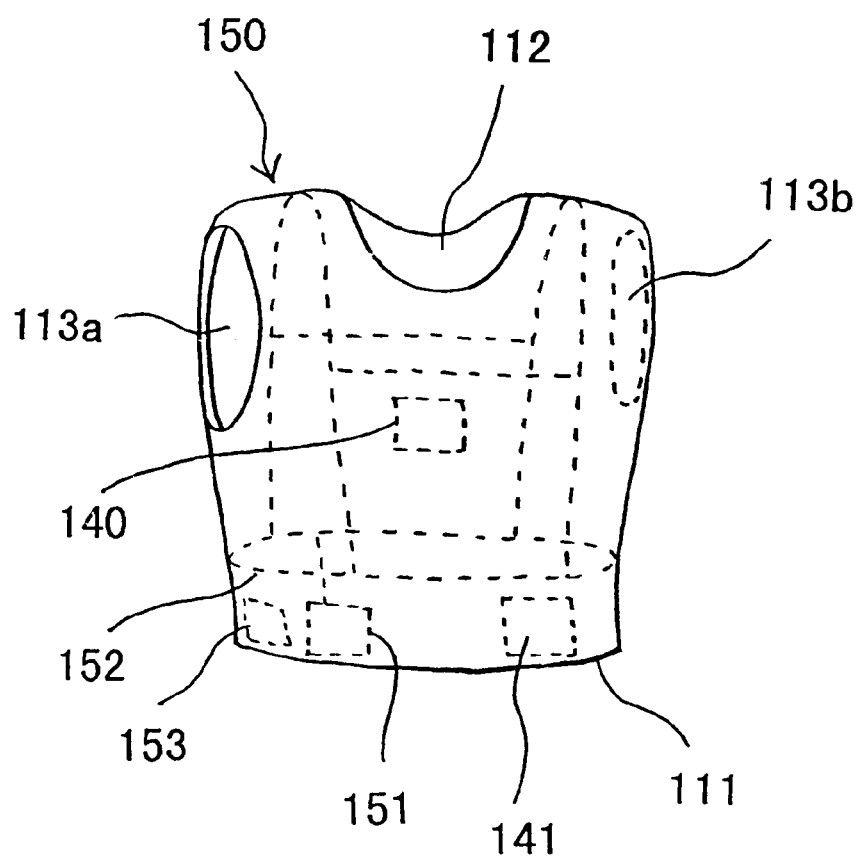
FIG. 13 is a perspective view illustrating a variation of the cooling garment according to the second embodiment.

Next, a variation of the second embodiment will be described. FIG. 13 illustrates a cooling garment 150 which is a variation of the second embodiment. The same elements as those in the cooling garment of the second embodiment will be provided with the same reference numerals and will not be described below.

In the second embodiment, a fine fibrous material is used for the outside of the inner cloth 120 so as to diffuse water across the entire garment by utilizing the capillary phenomenon. However, water may not be spread uniformly across the entire inner cloth by the capillary phenomenon alone. In view of this, as illustrated in FIG. 13, the cooling garment 150 includes a water supply tube 152 provided across the entire garment as indicated by a dotted line, and water is supplied from a pump 151 attached on the back of the waist through the water supply tube 152 to the inner cloth 120. While the water supply tube 152 is provided along the fibrous material on the outer side of the inner cloth 120, the water supply tube 152 is provided as a very thin tube so as not to occlude the air passageways 122 between the inner cloth 120 and the outer cloth 121.

The water supply tube 152 is closed except for the portion via which it is connected to the pump 151, and many minute holes are provided along the path at intervals of about 10 cm, for example. The pump 151 is designed to supply water from a tank 153 to the water supply tube 152 in a pulsed manner at constant time intervals. When water is supplied from the pump 151 and the water pressure in the water supply tube 152 thereby momentarily increases, water oozes from the holes little by little in equal amounts to be supplied to the inner cloth 120. The supplied water radially diffuses about the hole by the capillary phenomenon of the inner cloth 120. Thus, water is reliably spread across the entire cooling garment 150. By setting the amount of water supplied to be about 1 cc per a-single supply and the number of times water is supplied to be about 17 per hour so that the amount of water vaporized per hour is about 17 cc, the resulting degree of cooling is as that with the cooling garment of the second embodiment.

As described above, the cooling garment according to the second embodiment and the cooling garment according to the variation thereof are based on the phenomenon that the water supplied to the inner cloth, upon vaporization, takes the vaporization heat away from the ambient. Therefore, the structure is very simple and thus it can be produced at a low cost. Moreover, as compared to an air conditioner, a sufficient cooling can be obtained with a much smaller power consumption. Furthermore, unlike other devices such as air conditioners, it can be used outdoor as well as Indoor, whereby it is very useful when having an outdoor activity during a hot season such as in the midsummer.

Figure 14:
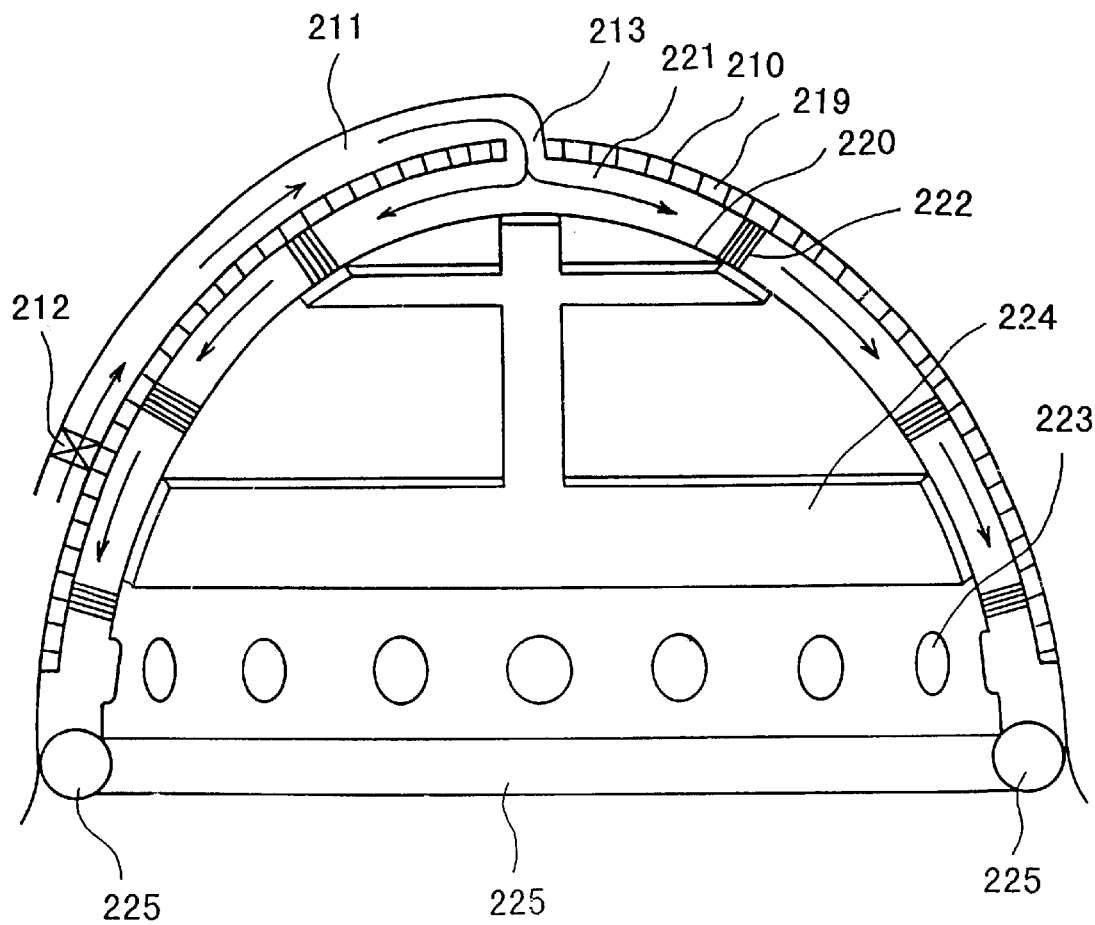
FIG. 14 is a cross-sectional view illustrating a cooling helmet according to the third embodiment.

Next, a cooling helmet of the third embodiment of the present invention will be described with reference to the figures. FIG. 14 is a cross-sectional view illustrating a cooling helmet according to the third embodiment. In the figure, an outer shell 210 is provided for protecting the head, and is obtained by molding a material having a sufficient strength. A duct 211 for introducing air is provided on the outer shell 210. The duct 211 is provided to extend from the top portion of the helmet in a front and downward direction. A fan 212 is provided in the vicinity of the tip portion of the duct 211, and the air is sucked in through the tip portion of the duct 211 by rotating the fan 212. The fan 212 corresponds to the air supply means of the present invention.

A hole 213 is provided at the top portion of the outer shell 210 for connecting the duct 211. The air which has been sucked in by the fan 212 and passed through the duct 211 is introduced into the outer shell 210 via the hole 213.

A thermal insulator material 219 is attached substantially across the entire surface on the inner side of the outer shell 210. This is for maintaining as much as possible the temperature inside the helmet lower than the outside temperature so as to further enhance the cooling efficiency based on a principle to be described later. Inside the thermal insulator material 219, a water guiding sheet 220 is provided to cover the entire head of a person who wears the helmet. Note that a space defining an air passageway 221 is provided by spacers 222 between the water guiding sheet 220 and the thermal insulator material 219. Openings 223 are provided substantially along the entire circumference in the vicinity of the lower end portion of the water guiding sheet 220. They serve as discharge ports for discharging the air which has been sucked in by the fan 212 and introduced into the outer shell 210 through the duct 211 and the hole 213. As described above, when the openings 223 are provided in the lower end portion of the water guiding sheet 220, the air is discharged to the inside of the helmet. Alternatively, instead of providing the openings in the water guiding sheet 220, the openings may be provided along the circumference of the lower end portion of the outer shell 210 so that the air is discharged to the outside.

The water guiding sheet 220 is sufficiently wet on the side close to the air passageway 221 (the outer side), but is completely dry on the other side close to the head (the inner side). Therefore, when the helmet is worn, the head would not become wet. The water guiding sheet 220 may be obtained by using separate materials for the outer side and the inner side, respectively, by combining, for example, a gauze cloth which is easily permeated by water and a water-impermeable polyethylene cover so that the gauze cloth material is on the outer side with the polyethylene cover being on the inner side.

A supporting strip 224 which is made by knitting together strip-shaped cloths each made of a meshed material is provided on the inner side of the water guiding sheet 220. When the helmet is-worn, the supporting strip 224 is in contact with the head of the wearer, and the load of the helmet acts upon the head of the wearer via the supporting strip 224.

In the lower end portion of the helmet, a ring-shaped sponge 225 which is made of a PVA (polyvinyl alcohol) is provided around the perimeter of the outer shell 210. The sponge 225 is held by being just fit into the annular groove which is formed by folding back the lower end portion of the water guiding sheet 220 to the outside. The tip portion of the folded water guiding sheet 220 is secured to the lower end portion of the outer shell 210.

The sponge 225 is capable of holding water in an amount of about 100 cc. When the sponge 225 is held by the water guiding sheet 220 as described above, the outer surface of the water guiding sheet 220 closely contacts with the sponge 225. Thus, the water held in the sponge 225 is sucked up by the capillary phenomenon of the fiber forming the water guiding sheet 220 and is spread across the entire water guiding sheet 220. Therefore, the entire surface of the outer side of the water guiding sheet 220 always remains wet.

The sponge 225 may be refilled with water through the openings 223 in the water guiding sheet 220 as described above. Alternatively, the sponge 225 may be detached from the helmet, allowed to absorb water, and then attached again to the original place.

Next, the principle based on which the cooling helmet of the present embodiment provides cooling will be described. With the water which has been sucked up from the sponge 225 being spread substantially across the entire water guiding sheet 220, the helmet is worn and the switch of the fan 212 is turned ON. Then, the outside air is introduced into the helmet from the duct 211 via the hole 213. The air flows to the lower side of the helmet through the air passageway 221 which is defined between the thermal insulator material 219 and the water guiding sheet 220, and is discharged through the openings 223. During the passage, the air closely contacts with the outer side of the water guiding sheet 220, thereby promoting vaporization of the moisture containing in the water guiding sheet 220. The vaporized moisture is carried to the outside through the openings 223 along with the air passing therethrough.

A liquid, upon vaporization Into gaseous molecules, takes the vaporization heat away from the ambient. Therefore, the temperature of the moisture held in the water guiding sheet 220 is lowered. The low temperature cools the head which is located very close to the water guiding sheet 220. Thus, the head of a person wearing the helmet via the water guiding sheet 220 is cooled. The cooling effect provided by the vaporization heat is quite significant. Therefore, even when working during a hot midsummer day, one can feel a significant coolness or coldness if one wears the cooling helmet of the present embodiment. Thus, it is possible to effectively prevent the exhaustion of stamina, lowering of concentration, and lowering of work efficiency.

As in the embodiments described above, it can be said that such a cooling principle based on the heat of vaporization of water is an application of the perspiration-based cooling function inherent to higher animals, that is, the function of perspiring when it is hot so as to cool the body by the vaporization heat which is taken away upon vaporization of the moisture. In addition, in the system of the present embodiment, the amount of vaporization of water (corresponding to the amount of perspiration of animals) can be freely controlled by varying the amount of air flow. The adjustment of the amount of air can be done by turning a volume control (not shown) which is connected between the fan and the power source. The battery (not shown) to serve as a power source for the fan may be attached to the helmet itself, or may alternatively be held in a position around the waste, for example, while being accommodated in an appropriate case, in which case it is connected to the helmet via a conductive line.

Moreover, the vaporization heat which is taken away upon perspiration of people or animals lowers not only the temperature of the skin but also the temperature of the evaporated and vaporized moisture. The cooled moisture has substantially no contribution to the cooling of the body but is directly dissipated into the air. In contrast, with the system of the present embodiment, the air which has been cooled simultaneously with the vaporization flows very close to the head, whereby the temperature gradient in the vicinity of the head is very large. If the temperature gradient is large, the heat radiation from the head is promoted, whereby an additional coolness is felt by a person. Moreover, since the cooled air is discharged through the openings 223 to the inside of the helmet, there is added the refreshing coolness from the air blown against the head and the face.

As mentioned above, vaporization of 1 cc of water takes away a heat of about 580 calories. Therefore, even if only a little water is vaporized per unit time, there is provided a sufficient cooling effect. Moreover, since the amount of water required to be vaporized per unit time is very small, the fan can be a very small fan, and it is thereby possible to suppress the power consumption. Thus, the duration of the battery is considerably long.

Next, a variation of the third embodiment of the present invention will be described. The cooling helmet according to this variation is characterized in that the cooling helmet can be made from a commercially available safety helmet. Therefore, the production method therefor will be focused on in the following description.

Figure 15:
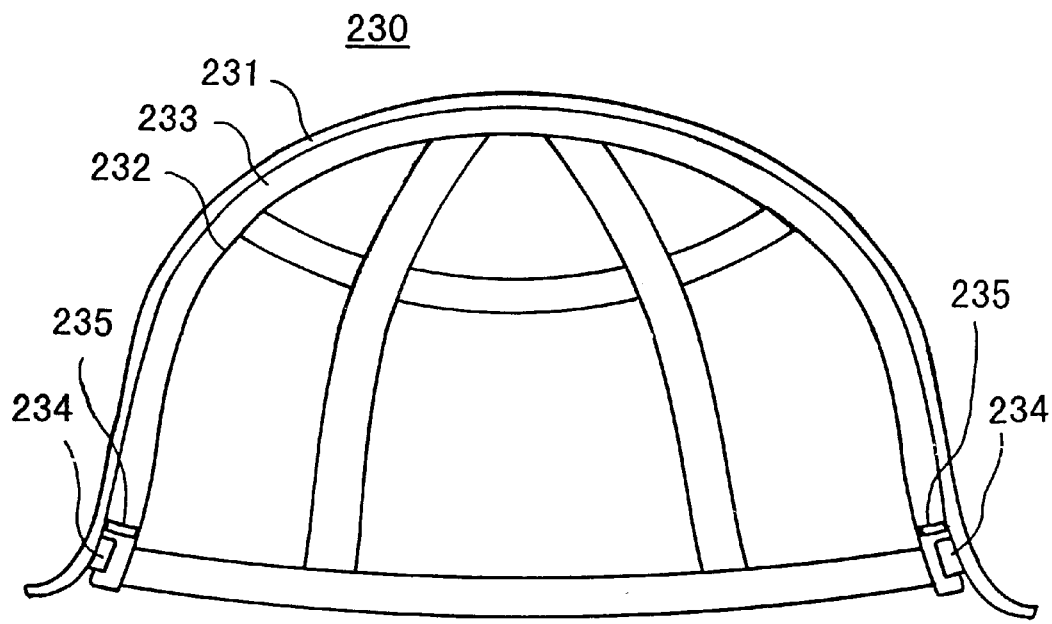
FIG. 15 is a cross-sectional view illustrating a common safety helmet.

FIG. 15 is a cross-sectional view illustrating one of the most common safety helmets that are commercially available. As illustrated in the figure, a safety helmet 230 is composed of an outer shell 231 and a head holding band 232 on the inner side of the outer shell 231. The head holding band 232 is obtained by knitting together strip-shaped cloths into a shape such as to cover the head when the helmet is worn, and is secured to the outer shell 231 by metal fittings 234 on the inner side of the lower end portion of the outer shell 231. A spacer 235 is provided in the vicinity of the metal fittings 234 of the head holding band 232 to keep a constant interval between the head holding band 232 and the inner side of the outer shell 231. This is for preventing the head from hitting the outer shell 231 when wearing the helmet 230 or even when the helmet being worn is hit by something from the outside. A space 233 between the head holding band 232 and the inner side of the outer shell 231 serves as an air passageway which is formed upon attachment of a water guiding sheet to be described later. To wear the helmet 230, chords extending from the head holding band 232 are tied together under the chin by a buckle to secure the helmet 230 to the head.

Since the metal fittings 234 illustrated in FIG. 15 is detachable, the head holding band 232 can be detached from the outer shell 231. While a hole as that illustrated in FIG. 14 is actually provided at the top portion of the outer shell 231 and a duct and a fan are further provided, these elements are omitted in FIG. 15.

Figure 16:
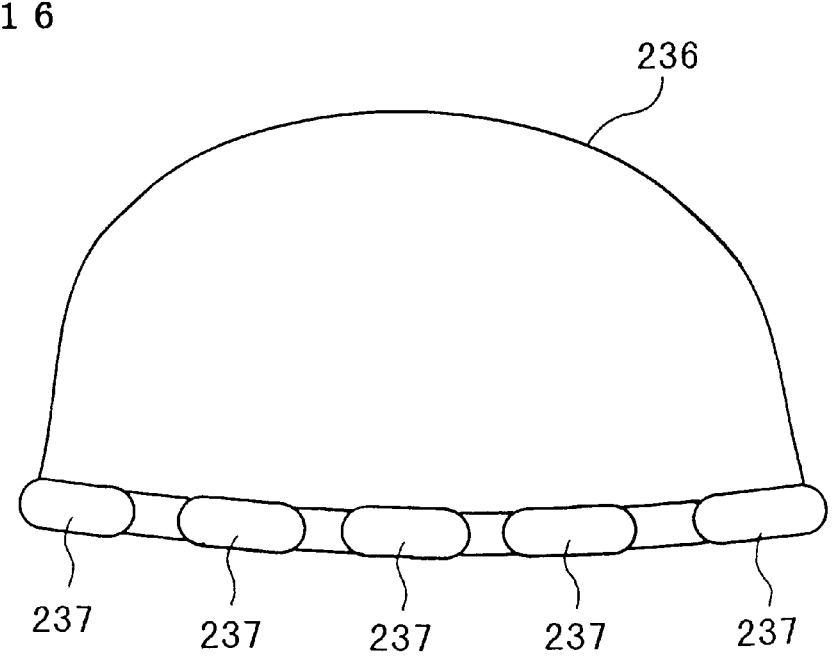
FIG. 16 is a side view illustrating a water guiding sheet to be attached to the safety helmet illustrated in FIG. 15.

A water guiding sheet 236 illustrated in FIG. 16 is laid over the outer side of the head holding band 232 which has been detached from the outer shell 231. The shape and size of the water guiding sheet 236 are set to be slightly larger than the head holding band 232 in view of the fact that the water-guiding sheet 236 is laid over the outer side of the head holding band 232 A portion of the water guiding sheet 236 which corresponds to the metal fittings 234 is notched so as not to interfere with the attachment/detachment of the metal-fittings 234. In such a state, the head holding band 232 is placed back into the outer shell 231, and the head holding band 232 covered by the water guiding sheet 236 is secured to the outer shell by the metal fittings 234.

A sponge 237 made of a PVA capable of containing water therein is provided as water supply means in the lower end portion of the water guiding sheet 236. While an annular sponge is provided substantially along the entire circumference of the lower end portion in the embodiment illustrated in FIG. 14, sponges each having a length of about a few centimeters are arranged at constant intervals in this variation.

In the cooling helmet of the third embodiment illustrated in FIG. 14, the fan is designed so as to suck in the outside air through the tip portion of the duct to feed the air from the top portion of the outer shell into the helmet. This variation, on the contrary, employs a structure in which air is sucked up from the inside of the helmet and the air is discharged to the outside through the top portion of the helmet. When the fan is rotated, the outside air is sucked in through the gap between the sponges 237. Then, the air flows upward through the air passageway 233 between the water guiding sheet 236 and the outer shell 231, and is eventually discharged to the outside through the hole at the top portion of the outer shell 231. The principle that the passage of the air through the air passageway 233 promotes vaporization of water contained in the water guiding sheet, thereby cooling the head, is as described above in the third embodiment, and thus will not be specifically described below.

Allowing the air to flow in the bottom-to-top direction through the helmet as described above has the following advantages. While the water guiding sheet 236 sucks up the water contained in the sponge 237 by the capillary phenomenon in the bottom-to-top direction, the water moves upward against the gravity. Therefore, the amount of water contained in the water guiding sheet 236 is larger in the lower end portion where the sponge 237 is provided and is smaller in a position closer to the top portion. On the other hand, the humidity of the air introduced into the air passageway gradually increases by vaporization of water while the air flows through the air passageway, with the capability of vaporizing water gradually decreasing. Therefore, when the air is allowed to pass in the bottom-to-top direction, more water is vaporized in the lower end portion where there is more moisture, and the amount of water vaporized decreases in a position closer to the top portion where there is less moisture. Thus, by allowing the air to flow in the bottom-to-top direction through the helmet, the amount of water vaporized can be varied in an efficient manner according to the amount of water contained in the water guiding sheet 236.

Next, another variation of the third embodiment will be described. By wearing the cooling helmet of the embodiment described above or that of the first variation, it is possible to ensure a coolness in the head during work. However, one would sweat in the head during an outdoor hard labor in a hot midsummer period. Therefore, in order to effectively vaporize the sweat, a small air hole is provided in a portion of the water guiding sheet of the embodiment described above or that of the first variation which corresponds to the top of the head.

In this way, in the case of the third embodiment, the air sucked in from the outside by the fan is not only supplied to the air passageway but is also blown directly onto the head of the wearer, and the air flows downward between the head and the water guiding sheet. In the case of the cooling helmet of the first variation, the fan sucks in the air, whereby the air not only flows upward through the air passageway but also flows upward between the head of the wearer and the water guiding sheet.

By such an air flow, the sweat of the wearer on the head is effectively vaporized upon which the vaporization heat is taken away. Therefore, an additional coolness is felt by the wearer due to the vaporization of the sweat on the head as well as the vaporization of the water which is contained in the water guiding sheet. Moreover, the vaporization of the sweat also eliminates the discomfort around the head due to the humidity from the sweat. Thus, it is possible to effectively prevent the lowering of concentration during work, thereby improving the work efficiency.

In such a case, since the amount of air flowing between the head and the water guiding sheet depends upon the size of the air hole, it is desirable to experimentally determine the optimal size of the air hole for each particular application.

Various modifications other than those described above can be made to the third embodiment, and they also fall within the technical scope of the present invention.

For example, while the duct is provided along the outer shell with the fan being provided in the vicinity of the tip portion thereof so that the outside air is sucked in therethrough in the embodiment described above, it is alternatively possible to employ a structure in which a fan is provided in the vicinity of the top portion of the outer shell, for example, while omitting the duct. Moreover, while the sponge as the water supply means is provided along the lower circumference of the outer shell in the embodiments described above, it may alternatively be provided in the vicinity of the top portion of the outer shell, for example. Furthermore, the water supply means may be provided as a container of a plastic, or the like, which is provided in the lower end portion of the helmet or the outer side of the outer shell, with water therein, while the water guiding sheet is immersed therein.

Moreover, while the above embodiment has been described primarily with respect to a safety helmet, it is understood that the present invention is also applicable to various other helmets such as a motorcycle helmet. Furthermore, other than safety or motorcycle helmets, the present invention is also applicable to an ordinary headpiece by providing the headpiece with a member having some degree of strength which corresponds to the outer shell of a helmet while also providing it with the water supply means and the air supply means. Then, it can be used as a headpiece for cooling the head when having an outdoor activity in a hot season.

In the case of a motorcycle helmet, the fan as the air supply means can be omitted. Specifically, the motorcycle helmet is provided with an air inlet so as to take in the air through the air inlet by utilizing the wind pressure which acts upon the helmet when riding the motorcycle and to guide the air into the air passageway provided with the water guiding sheet, thereby vaporizing the water which is contained in the water guiding sheet. In such a case, the air inlet serves as the air supply means. With such a structure, the fan and the power source for driving the fan are no longer necessary, thereby simplifying the structure and also reducing production cost.

As described above, with the cooling helmet according to the present invention, the head is cooled efficiently by utilizing the heat of vaporization of water. Therefore, even when having an outdoor work or riding a motorcycle in a hot summer period, the head is cooled so that one can feel cool, thereby effectively suppressing the exhaustion of stamina, lowering of concentration, lowering of work efficiency, etc.

INDUSTRIAL APPLICABILITY

As described above, according to the present invention, the ambient air is passed in the vicinity of the surface of the body, while the air is closely contacted with water being diffused over a wide area, thereby vaporizing the water. The temperature in the vicinity of the body surface is lowered based on the absorption of the vaporization heat which occurs when the water is vaporized, thereby forcibly increasing the temperature gradient to cool the body. The present invention is applicable to a pillow for ensuring a comfortable sleep in a hot and hard-to-sleep night, a garment, a helmet and a headpiece for allowing one to be comfortable even in a high temperature environment.

What is claimed is:

1. A cooling pillow, comprising:
   an air passageway serving as a path of air;
   a sheet-like water holding member provided on the air passageway for holding water with at least one side thereof which is in contact with the passageway being wet;
   air supply means for forcibly supplying air into the air passageway; and a water supply section for continuously supplying water to the water holding member by a water absorbing action of the water holding member, wherein a head which is rested on the water holding member directly or via a thermally conductive member is cooled by a vaporization heat which is absorbed upon vaporization of the water held in the water holding member into the air passing through the air passageway.

2. A cooling pillow according to claim 1, wherein the water holding member is detachably attached on the air passageway.

3. A cooling pillow according to claim 2, comprising control means for controlling an air supply capability of the air supply means.

* * * * *